United States Patent [19]

Sundeen et al.

[11] Patent Number: 4,680,388
[45] Date of Patent: Jul. 14, 1987

[54] O-SULFATED SPIRO β-LACTAM HYDROXAMIC ACIDS

[75] Inventors: Joseph E. Sundeen, Yardley, Pa.; William H. Koster, East Amwell Township; Hunterdon County; Robert Zahler, Princeton, both of N.J.

[73] Assignee: E. R. Squibb & Sons, Inc., Princeton, N.J.

[21] Appl. No.: 891,494

[22] Filed: Jul. 31, 1986

Related U.S. Application Data

[62] Division of Ser. No. 728,432, Apr. 29, 1985, Pat. No. 4,638,060.

[51] Int. Cl.$^4$ ............... C07D 487/10; C07D 491/107; C07D 495/10; C07D 471/10
[52] U.S. Cl. ..................... 540/203; 514/210; 560/27; 560/121; 560/123; 562/450; 562/503; 562/505; 564/300; 549/65; 549/419
[58] Field of Search ................... 540/203; 514/210

[56] References Cited

U.S. PATENT DOCUMENTS 4,260,743  4/1981  Bose ............................... 260/239 A
4,337,197  6/1982  Gordon et al. ...................... 540/355

OTHER PUBLICATIONS

Toyama et al, Chemical Abstracts 100:68066q, (1984).
Japanese Patent Publication 58/113174, (1983).
Aue et al, Tetrahedron Letters, 1973, 3719, Aue et al., "Additions to Cyclobutenes: Synthesis of 5—Azabicyclo[2.1.0]Pentanes, 2—Azabicyclo[2.2.0]Hexanes, and 1—Azaspiro[3.3]Heptanes".
Manhas et al, Tetrahedron, 25:4421, (1969), "Studies on Lactams—XII".
Bose et al, Tetrahedron, 37:2321, (1981).
Hassan et al, Zh. Naturforsch, 33b:1515, (1978), "Synthesis of Some New Spiro Heterocyclic Nitrogen Compounds, II".
Hassan et al, J. Prakt. Chemie, 321:870, (1979), "A Convenient Synthesis of Spiro Heterocyclic Compounds".
Bose et al, Tetrahedron Letters, 40:3547, (1974), "β—Lactams Via Cycloaddition to Iminomalonates".

Primary Examiner—Mark L. Berch
Attorney, Agent, or Firm—Lawrence S. Levinson; Donald J. Barrack

[57] ABSTRACT

Antibacterial activity is exhibited by compounds having the formula

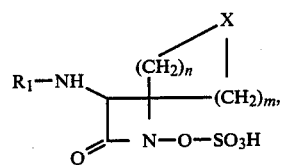

and pharmaceutically acceptable salts thereof.

6 Claims, No Drawings

O-SULFATED SPIRO β-LACTAM HYDROXAMIC ACIDS

This is a division of application Ser. No. 728,432, filed Apr. 29, 1985, now U.S. Pat. No. 4,638,060.

Antibacterial activity is exhibited by β-lactam compounds having the formula

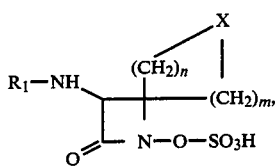

and pharmaceutically acceptable salts thereof.

In formula I, and throughout the specification, the symbols are as defined below.

$R_1$ is acyl; and n and m are each independently 1, 2 or 3 and X is a saturated carbon to carbon bond; n and m are each indpendently 1, 2, 3 or 4, the sum of $n+m \leq 5$ and X is —O—, —S—,

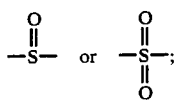

n and m are each independently 1, 2 or 3, the sum of $n+m \leq 4$ and X is

(wherein $R_2$ is alkyl, aryl, hydroxy, alkoxy, alkanoyloxy, carbamoyloxy, alkanoylamino, or ureido) or

(wherein $R_3$ is hydrogen, alkyl, aryl, alkanoyl or carbamoyl); n and m are each independently 1 or 2, the sum of $n+m \leq 3$ and X is

(wherein $R_4$ is hydrogen, alkyl or aryl); or n and m are each 1 and X is —S—CH$_2$—S—,

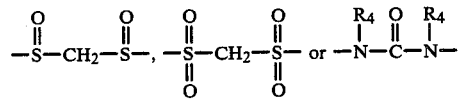

(wherein $R_4$ is hydrogen, alkyl or aryl).

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkanoyl" refers to both straight and branched chain groups. Those groups having 2 to 10 carbon atoms are preferred.

The term "aryl" refers to phenyl and phenyl substituted with 1, 2 or 3 amino, halogen, hydroxyl, trifluoromethyl, alkyl of 1 to 4 carbons, alkoxy of 1 to 4 carbons, alkanoyloxy, aminocarbonyl, or carboxy groups.

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, British Pat. No. 1,348,894, published Mar. 27, 1974, and European patent application 75,805, published Apr. 6, 1983. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

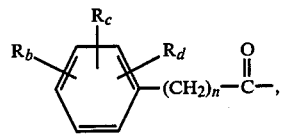

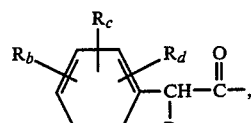

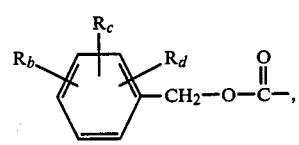

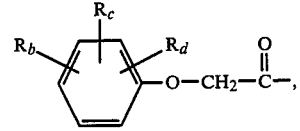

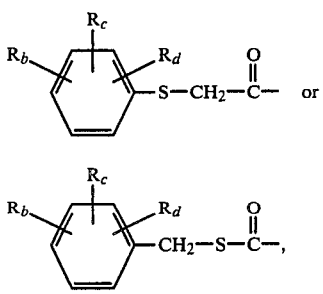

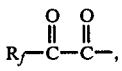

wherein n is 0, 1, 2 or 3; $R_e$ is as defined above; and $R_f$ is a substituted or unsubstituted 5-, 6- or 7-membered heterocyclic ring containing 1,2,3, or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

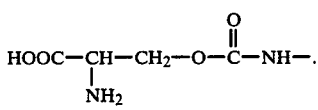

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

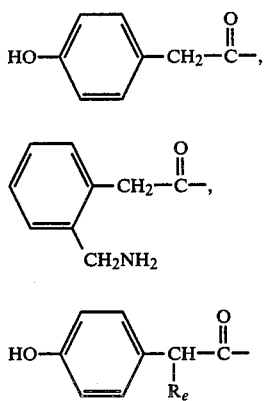

($R_e$ is preferably a carboxyl salt or sulfo salt) and

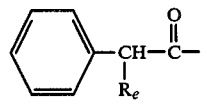

($R_e$ is preferably a carboxyl salt or sulfo salt).

(c) Heteroaromatic groups having the formula

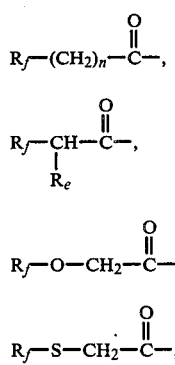

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

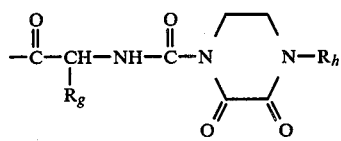

wherein $R_g$ is an aromatic group (including carbocyclic aromatics such as those of the formula

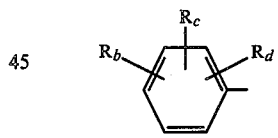

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ is as defined above), arylcarbonylamino (i.e.,

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

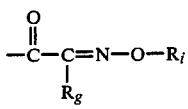

wherein $R_g$ is as defined above and $R_i$ is hydrogen, alkyl, cycloalkyl, alkylaminocarbonyl, arylaminocarbonyl (i.e.,

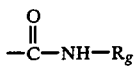

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

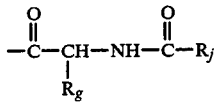

wherein $R_g$ is as defined above and $R_j$ is

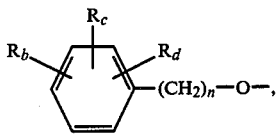

amino, alkylamino, (cyanoalkyl)amino, amido, alkylamido, (cyanoalkyl)amido,

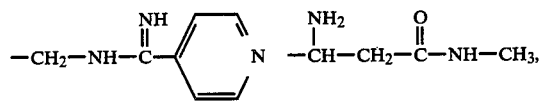

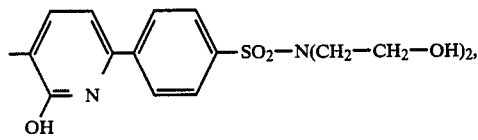

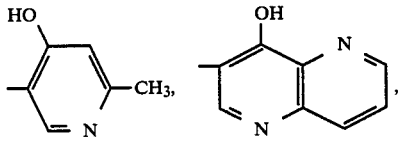

-continued

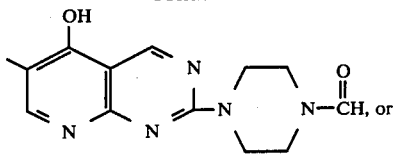

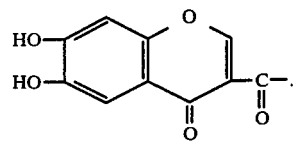

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

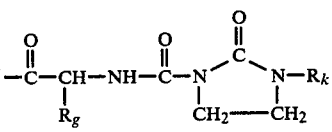

wherein $R_g$ is as defined above and $R_k$ is hydrogen, alkylsulfonyl, arylmethyleneamino (i.e., $-N=CH-R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with inorganic and organic bases which are also within the scope of this invention. Such salts include ammonium salts, alkali metal salts, alkaline earth metal salts, and salts with organic bases such as dicyclohexylamine, benzathine, N-methyl-D-glucamine, hydrabamine and the like.

The compounds of this invention are pictured as acids. They can also exist, however, as zwitterions (internal or inner salts), and these are also included within the language "pharmaceutically acceptable salts" and the scope of this invention.

DETAILED DESCRIPTION OF THE INVENTION

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be adminsitered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular and as a suppository.

The compounds of this invention can be prepared utilizing as starting materials a protected amino acid ester having the formula

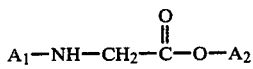
II and a ketone having the formula

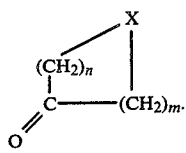
III

In formula II, and throughout the specification, the symbol $A_1$ refers to an amino protecting group (e.g., t-butoxycarbonyl, benzyloxycarbonyl, etc.) and the symbol $A_2$ refers to a carboxyl protecting group (e.g., alkyl, benzyl, or benzhydryl). An aldol condensation of a compound of formula II with a ketone of formula III yields the corresponding compound having the formula

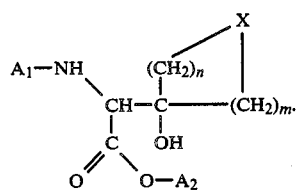
IV

Removal of the carboxyl protecting group "$A_2$" using standard deprotection techniques yields the corresponding compound having the formula

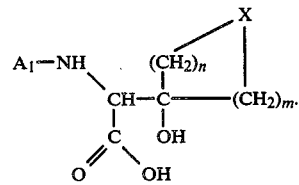
V

Coupling an acid of formula V with an O-protected hydroxylamine, having the formula

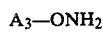
VI wherein $A_3$ is a protecting group such as benzyl, trityl or pivaloyl, yields the corresponding compound having the formula

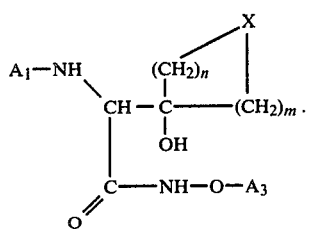
VII

The reaction proceeds in the presence of a coupling agent such as 1-ethyl-3-(dimethylaminopropyl)carbodiimide or dicyclohexylcarbodiimide.

Cyclization of a compound of formula VII can be accomplished by treating the compound with triphenylphosphine and a dialkylazodicarboxylate to yield the corresponding compound having the formula

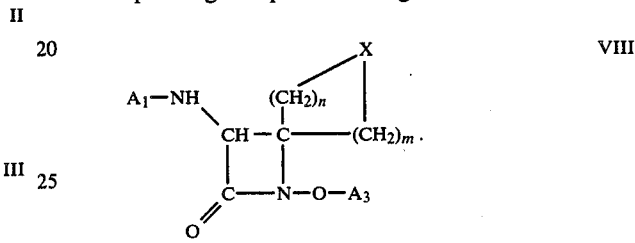
VIII

Alternatively, a compound of formula VIII can be prepared by first converting the hydroxyl group of a compound of formula VII to a leaving group (e.g., using a reagent such as pyridine-sulfur trioxide complex) and subsequently treating that compound with base (e.g., an alkali metal carbonate).

Reduction of a compound of formula VIII to the corresponding compound having the formula

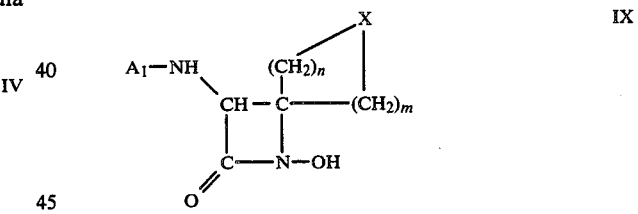
IX can be accomplished by catalytic hydrogenation if $A_3$ is benzyl, treatment with a base such as sodium sulfide or sodium hydroxide if $A_3$ is pivaloyl, or by treatment with 80% aqueous acetic acid if $A_3$ is trityl.

A compound of formula IX can be treated with a complex of pyridine and sulfur trioxide to yield the pyridinium salt of the compound having the formula

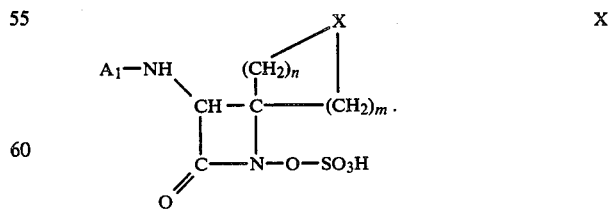
X

The reaction can be run in an organic solvent, preferably pyridine. Instead of using a pre-formed complex of pyridine and sulfur trioxide, the complex can be formed in situ (e.g., using chlorosulfonyltrimethylsilyl ester and pyridine as reagents). Alternatively, a complex of dimethylformamide-sulfur trioxide or 2,6-lutidine-sulfur trioxide can be used. Using conventional techniques (e.g., ion-exchange resins, crystallization or ion-pair extraction) the pyridinium salt formed by the above reactions can be converted to other salts.

Deprotection of the 3-amino substituent of a compound of formula X can be accomplished using standard deprotection techniques and yields the corresponding compound having the formula

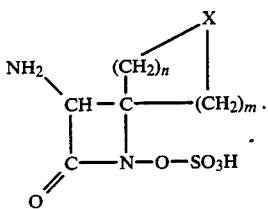

If, for example, the protecting group is t-butoxycarbonyl, trifluoroacetic acid can be used to deprotect the amino group. If the protecting group is benzyloxycarbonyl, catalytic hydrogenation can be used. If the protecting group is o-nitrosulfenyl, p-toluenesulfonic acid can be used in combination with p-thiocresol.

Well-known acylation techniques can be used to convert a compound of formula XI to a product of formula I. Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group ($R_1$) contains reactive functionality (such as amino or carboxyl groups) it may be necessary to first protect these functional groups, then carry out the acylation reaction, and finally deprotect the resulting product.

Alternative techniques for preparing the compounds of this invention will be apparent to the practitioner of this invention. For example, the amino protecting group can be removed from a compound of formula VIII and the resultant compound acylated before removing the oxygen protecting group ("$A_3$") in the 1-position of the $\beta$-lactams and sulfonating.

The preferred acyl ("$R_1$") groups of this invention are those having the formula

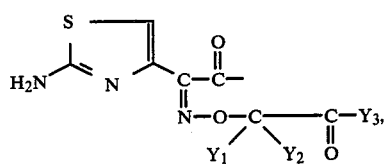

wherein $Y_1$ and $Y_2$ are each independently hydrogen or methyl or $Y_1$ and $Y_2$ together with the carbon atom to which they are attached are cyclopropyl, cyclobutyl or cyclopentyl and $Y_3$ is hydroxy, amino or hydroxyamino.

The compounds of formula I contain at least one chiral center—the carbon atom (in the 3-position of the $\beta$-lactam nucleus) to which the amino or acylamino substituent is attached. This invention is directed to those $\beta$-lactams which have been described above, wherein the stereochemistry at the chiral center in the 3-position of the $\beta$-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

The following examples are specific embodiments of this invention.

EXAMPLE 1

(Z)-[[[1-(2-Amino-4-thiazolyl)-2-oxo-2-[[2-oxo-1-(sulfooxy)-1-azaspiro[3.4]oct-3-yl]amino]ethylidene]amino]oxy]acetic acid, dipotassium salt (A) N-(t-Butoxycarbonyl)glycine, benzyl ester N-(t-Butoxycarbonyl)glycine (8.75 g, 0.05 mole) and benzyl bromide (9.4 g, 0.055 mole) were slurried in 20 ml of dimethylformamide and treated with 6.0 g (0.06 mole) of potassium bicarbonate under argon. After stirring for 38 hours, water was added to give a mass of chunky white solid which was filtered and washed with water. The solid was taken up in ethyl acetate, dried (sodium sulfate), evaporated to a solid, and recrystallized from 600 ml of hot hexane. Cooling to −5° C. for two hours and filtering gave 11.6 g of crystalline flakes, melting point 72°–73° C., in two crops.

(B) N-(t-Butoxycarbonyl)-α-(1-hydroxycyclopentyl)glycine, benzyl ester

A solution of diisopropylamine (3.77 ml, 23 mmole) in 40 ml of dry tetrahydrofuran under argon was chilled to −40° C. and treated with 13 ml of a 1.71 N n-butyllithium solution (21.5 mmoles). After stirring for 20 minutes, the mixture was cooled to −78° C. and treated with a solution of N-(t-butoxycarbonyl)glycine, benzyl ester (2.65 g, 10 mmole) in 10 ml of tetrahydrofuran. The mixture became darker yellow, but remained clear. After 0.5 hours at −78° C., 0.88 ml (11.5 mmoles) of dried (4Å sieves) cyclopentanone was added and then after 15 minutes at −78° C., the mixture was warmed over 0.5 hours to −20° C., whereupon the solution darkened to a deep purple. The temperature was raised to 0° C. for 20 minutes, then 1.32 g (22 mmole) of acetic acid in 5 ml of tetrahydrofuran was added, whereupon the color was discharged, leaving a gelatinous precipitate. The mixture was poured into water and extracted with ethyl acetate. The organic layer was washed with brine, dried (sodium sulfate) and evaporated to an oil which was chromatographed on 900 ml of LPS-1 in hexane:ethyl acetate, 3:1. Evaporation of product fractions and crystallization from hexane gave, in two crops, 1.68 g of product, melting point 68°–70° C. (Rf=0.77, silica, hexane:ethyl acetate, 3:1).

(C) N-(t-Butoxycarbonyl)-α-(1-hydroxycyclopentyl)glycine

A solution of N-(t-butoxycarbonyl)-α-(1-hydroxycyclopentyl)glycine, benzyl ester (1.81 g, 4.98 mmoles) in 30 ml of absolute ethanol at 25° C. was treated with 0.4 g of 10% palladium on charcoal and hydrogen at one atmosphere for 2.5 hours. The catalyst was filtered and the solvent evaporated. Benzene was added and evaporated. Crystallization from isopropyl ether (first crop) and hexane (second crop) gave a total of 1.07 g of product, melting point 132°–134° C.

(D)
N-(Benzyloxy)-N²-(t-butoxycarbonyl)-α-(1-hydroxycyclopentyl)glycinamide

To a solution of N-(t-butoxycarbonyl)-α-(1-hydroxycyclopentyl)glycine (0.83 g, 3.2 mmole) in 20 ml of tetrahydrofuran under argon at 0° C. was added hydroxybenzotriazole monohydrate (0.43 g, 3.2 mmole) followed by the addition of dicyclohexylcarbodiimide (0.65 g, 3.2 mmole). The reaction mixture was stirred at 0° C. for two hours. A solution of o-benzylhydroxylamine hydrochloride (1 g, 6.3 mmole/10 ml water) was adjusted to pH 13 with 10% sodium hydroxide. Sodium chloride was added to saturation, and the free base was extracted into diethyl ether. After drying over anhydrous sodium sulfate, the ether was evaporated to give 0.8 g of the free amine as an oil. A solution of the o-benzylhydroxylamine in tetrahydrofuran was added to the hydroxybenzotriazole ester. The reaction mixture was warmed to 20° C. and stirred for 5 hours.

The reaction mixture was then cooled and filtered. The filtrate was evaporated to a foam which was dissolved in ethyl acetate and washed consecutively with water, 5% sodium bicarbonate and brine. After drying over anhydrous sodium sulfate, the solution was evaporated to an oil. The oil was then chromatographed on LPS-1 eluting with hexane:diethyl ether:methylene chloride (1:1:1). The fractions containing pure product were combined and evaporated yielding 0.82 g of solid product.

(E)
1-(Benzyloxy)-3-[(t-butoxycarbonyl)amino]-2-oxo-1-azaspiro[3.4]octane

To a solution of N-(benzyloxy)-N²-(t-butoxycarbonyl)-α-(1-hydroxycyclopentyl)glycinamide (0.82 g, 2.16 mmole) in 15 ml of pyridine under argon was added pyridine-sulfur trioxide complex (0.47 g, 29.5 mmole). The reaction mixture was heated at 50°–55° C. After 1.5 hours, an additional amount (0.150 g, 0.9 mmole) of pyridine-sulfur trioxide complex was added and the reaction was heated for an additional hour. The reaction mixture was then concentrated in vacuo and azeotroped three times with acetonitrile. To this residue was added a cold mixture of potassium carbonate solution (3.32 g/9 ml water) and ethyl acetate (25 ml). The reaction was stirred vigorously and refluxed for two hours at which point tlc indicated that the reaction was near completion. After cooling, the reaction mixture was diluted with water and ethyl acetate and the phases separated. The organic phase was washed with 5% potassium bisulfate solution and brine and dried over anhydrous sodium sulfate. After evaporating to a residue, the crude benzyl ether was chromatographed on LPS-1 (hexane:ethyl acetate, 3:1) to give 550 mg of pure material.

(F)
3-[(t-Butoxycarbonyl)amino]-2-oxo-1-(sulfooxy)-1-azaspiro[3.4]octane, monopotassium salt A solution of 1-(benzyloxy)-3-[(t-butoxycarbonyl)amino]-2-oxo-1-azaspiro[3.4]octane (0.45 g, 1.29 mmole) in 25 ml of absolute ethanol was treated with 100 mg of 10% palladium on charcoal and stirred under an atmosphere of hydrogen at room temperature for one hour at which time tlc indicated no remaining starting material. After filtering through a bed of Celite and concentrating in vacuo to a residue, 10 ml of pyridine was added and the solution was cooled to 0° C. and stirred under argon. Three equivalents of pyridine-sulfur trioxide complex (643 mg) were added and the reaction was stirred at ambient temperature. After two hours, tlc indicated that the reaction was completed. After concentrating in vacuo, the residue was taken up in 10% dibasic potassium phosphate solution with a small amount of acetone to solubilize and placed on a Dowex AG-50 K+) column and eluted with water followed by 20% acetone/water. The fractions containing product were lyophilized and then purified on an HP-20 column eluting with water, followed by a 0–10% acetone/water gradient. Fractions containing product were lyophilized to give a total of 259 mg of product.

(G)
(Z)-[[[1-(2-Amino-4-thiazolyl)-2-oxo-2-[[2-oxo-1-(sulfooxy)-1-azaspiro[3.4]oct-3-yl]amino]ethylidene]amino]oxy]acetic acid, diphenylmethyl ester, monopotassium salt 3[(t-Butoxycarbonyl)amino]-2-oxo-1-(sulfooxy)-1-azaspiro[3.4]octane, monopotassium salt (280 mg, 0.75 mmoles) was covered with 2 ml of dry dichloromethane, 0.8 ml of anisole was added, and the mixture cooled to −10° C. Trifluoroacetic acid (3 ml) was added, and the solution was stirred at −10° to −5° C. for 1.5 hours. After 0.75 hours a solid formed, becoming quite substantial by 1.5 hours. The volatiles were evaporated in vacuo and the solid residue triturated with ether to give 3-amino-2-oxo-1-(sulfooxy)-1-azaspiro[3.4]octane.

(Z)-2-Amino-α-[[[[(diphenylmethyl)oxy]carbonyl]methyl]oxy]imino]-4-thiazoleacetic acid, diphenylmethyl ester (310 mg, 0.75 mmoles) in 4 ml of dry dimethylformamide was treated with 115 μl (0.82 mmoles) of triethylamine, and the mixture cooled to −30° C. under argon. Diphenyl chlorophosphate (155 μl, 0.75 mmoles) was added, and the mixture was stirred at −30° to −20° C. for 1 hour, giving a solution of a mixed anhydride of the starting acid.

A solution of 3-amino-2-oxo-1-(sulfooxy)-1-azaspiro[3.4]octane in 2.5 ml of dimethylformamide was prepared. Triethylamine (500 μl, 3.6 mmoles) was added to the solution of the mixed anhydride at −30° C., followed by the solution of the β-lactam. The mixture was allowed to warm to −5° C. over 0.5 hours under argon. The mixture was evaporated in vacuo to a gum. This was taken up in acetone and diluted with an equal volume of water. The pH (3.45) was adjusted to 6.85 with potassium bicarbonate, and the solution was passed through a Dowex AG50 (K+) column, eluting with 50% acetone. The product fractions were evaporated to a slurry which was applied to a 80 ml HP-20 column and eluted with water, then an acetone gradient up to 50% acetone. Product fractions (37.5%–50% acetone) were combined and lyophilized to give 0.31 g of product, ir=1780cm$^{-1}$ as a white solid.

(H)
(Z)-[[[1-(2-Amino-4-thiazolyl)-2-oxo-2-[[2-oxo-1-(sulfooxy)-1-azaspiro[3.4]oct-3-yl]amino]ethylidene]amino]oxy]acetic acid, dipotassium salt (Z)-[[[1-(2-Amino-4-thiazolyl)-2-oxo-2-[[2-oxo-1-(sulfooxy)-1-azaspiro[3.4]oct-3-yl]amino]ethylidene]amino]oxy]acetic acid, diphenylmethyl ester, monopotassium salt (0.31 g, 0.46 mmole) was slurried in 6 ml of dry dichloromethane and 0.8 ml of anisole and cooled to −10° C.; trifluoroacetic acid (10 ml) was added. After one hour at −10° to 5° C., dry toluene (10 ml) was added, and the mixture was evaporated to near dryness in vacuo. The residue was washed with hexane, then taken up in water (pH=1.8) and quickly adjusted to pH 6.85 with dilute potassium bicarbonate. Chromatography on 60 ml of HP-20 in water gave pure product. Lyophilization gave 217 mg of the title compound as a white powder, melting point 230°–250° C. (dec).

Analysis calc'd for $C_{14}H_{15}N_5O_9S_2K_2.3.5$ mole of $H_2O$ C, 27.90; H, 3.68; N, 11.62; S, 10.64; K, 12.97. Found: C, 27.85; H, 3.61; N, 11.94; S, 10.37; K, 13.56.

EXAMPLE 2

(Z)-[[[1-(2-Amino-4-thiazolyl)-2-oxo-2-[[2-oxo-2-[[2-oxo-1-(sulfooxy)-1-azaspiro[3.3]hept-3-yl]amino]ethylidene]amino]oxy]acetic acid, dipotassium salt

(A)

N-(t-Butoxycarbonyl)-α-(1-hydroxycyclobutyl)glycine, benzyl ester

A solution of diisopropylamine (9.7 ml, 70 mmoles) in 150 ml of dry tetrahydrofuran at −40° C. under argon was treated with 39 ml (64.5 mmoles) of 1.71N n-butyllithium is hexane and the pale yellow solution stirred at −40° C. for 20 minutes. The solution was cooled to −78° C., and a solution of 7.95 g (30 mmoles) of N-(t-butoxycarbonyl)glycine, benzyl ester in 30 ml of dry tetrahydrofuran was dripped in over 5 minutes, resulting in a dark yellow solution, and, after 20 minutes, a slight turbidity. After 0.5 hours, a solution of 2.42 g (2.0 ml, 34.5 mmoles) of cyclobutanone in 30 ml of tetrahydrofuran was added. The resulting yellow turbid mixture was stirred at −78° C. for 15 minutes, then placed in a 0° C. ice bath for 2 hours. At an internal temperature of −25° C. (1 hour), the solution became clear, and at −15° C. turned dark purple. It was stirred at 0° C. for 0.5 hours, then treated with 3.96 g (66 mmoles) of glacial acetic acid in 15 ml of tetrahydrofuran, giving a turbid, light yellow mixture. This was poured into 500 ml of cold water and extracted twice with ethyl acetate. The extracts were washed with 2% potassium bisulfate, 5% sodium bicarbonate, and brine, dried (sodium sulfate) and evaporated to a thick oil. Chromatography on 800 ml of LPS-1 in hexane:ethyl acetate (2:1) and combination of the product fractions (Rf=0.29) gave 7.8 g of product as an oil.

(B)

N-(t-Butoxycarbonyl)-α-(1-hydroxycyclobutyl)glycine

N-(t-Butoxycarbonyl)-α-(1-hydroxycyclobutyl)glycine, benzyl ester (7.8 g, 23.3 mmoles) was hydrogenated at 1 atmosphere over 1.0 g of 10% palladium on charcoal in 150 ml of absolute ethanol for 4 hours at 25° C. The catalyst was filtered and the solvent evaporated in vacuo. Benzene was added and evaporated twice, to give 5.0 g of product as a hard foam.

(C)

N-(Benzyloxy)-N²-(t-butoxycarbonyl)-α-(1-hydroxycyclobutyl)glycinamide

N-(t-Butoxycarbonyl)-α-(1-hydroxycyclobutyl)glycine (5.0 g, 20.4 mmoles) was dissolved in 150 ml of dry tetrahydrofuran under argon. Hydroxybenzotriazole hydrate (3.12 g, 20.4 mmole) was added, and the mixture was chilled to 0° C., and then treated with 4.20 g (20.4 mmoles) of dicyclohexylcarbodiimide. After 1.75 hours at 0° C., a solution of O-benzylhydroxylamine in 15 ml of tetrahydrofuran was added, and the mixture stirred at 0°–25° C. for 17 hours. The tetrahydrofuran mixture was then chilled to 10° C. for 20 minutes and the resulting solids filtered and washed with dry tetrahydrofuran. The filtrate was evaporated and the residue taken up in ethyl acetate and washed quickly with 2% potassium bisulfate, brine, 5% sodium bicarbonate, and brine, then dried (sodium sulfate) and evaporated to a foam. Trituration with isopropyl ether gave 4.69 g of product as a white solid, melting point 95°–97° C.

(D)

1-(Benzyloxy)-3-[(t-butoxycarbonyl)amino]-2-oxo-1-azaspiro[3.3]heptane

N-(Benzyloxy)-N²-(t-butoxycarbonyl)-α-(1-hydroxycyclobutyl)glycinamide (3.50 g, 10 mmole) in 200 ml of dry tetrahydrofuran at 0° C. under argon was treated with 2.4 ml (15 mmole) of diethylazodicarboxylate, then with a solution of triphenylphosphine (5.2 g, 20 mmole) in 50 ml of tetrahydrofuran over 10 minutes, and the mixture stirred at 0° C. for one hour. The yellow color persisted so an additional 0.52 g (2 mmole) of triphenylphosphine was added. After 15 minutes, evaporation in vacuo gave an oil. Trituration with 100 ml of hexane:ethyl acetate (2:1) gave a white solid which was filtered. Chromatography of the filtrate on 800 ml of LPS-1 gave product fractions [Rf=0.8 in hexane:ethyl acetate (1:1)] contaminated with a close-running impurity which was removed by trituration with isopropyl ether, giving the product as a white solid, 1.07 g, melting point 156°–157° C.

(E)

3-[(t-Butoxycarbonyl)amino]-2-oxo-1-(sulfooxy)-1-azaspiro[3.3]heptane, monosodium salt 1-(Benzyloxy)-3-[(t-butoxycarbonyl)amino]-2-oxo-1-azaspiro[3.3]heptane (1.07 g, 3.22 mmoles) was hydrogenated at 1 atmosphere in 30 ml of absolute ethanol over 0.4 g of 10% palladium on charcoal for 3 hours at 25° C. The catalyst was filtered and the solvent removed in vacuo at 10° C. to give a solid. This was taken up in 19 ml of dry pyridine and treated with 1.44 g (9 mmoles) of pyridine-sulfur trioxide at 25° C. under argon. After 4 hours, the volatiles were removed in vacuo, the residue taken up in water, and the pH (5.40) adjusted to 6.45 with dilute sodium bicarbonate. Passing through a 40 ml Dowex AG50 (K+) column in water brought out product within 300 ml. Lyophilization gave a white solid, which was chromatographed on HP-20, first in water, then with a gradient increase of acetone (20%). Product fractions were lyophilized to give 0.75 g of product as a white powder.

(F)

(Z)-[[[1-(2-Amino-4-thiazolyl)-2-oxo-2-[[2-oxo-1-(sulfooxy)-1-azaspiro[3.3]hept-3-yl]amino]ethylidene]amino]oxy]acetic acid, diphenylmethyl ester, monopotassium salt 3-[(t-Butoxycarbonyl)amino]-2-oxo-1-(sulfooxy)-1-azaspiro[3.3]heptane, monosodium salt (0.3 g, 0.87 mmole) was slurried in 2.5 ml of dry dichloromethane and 1.0 ml of anisole at −10° C. under argon, and then treated with 4.0 ml of trifluoroacetic acid. After 0.5 hour, a solid had formed. After 1.5 hours, 4 ml of dry toluene was added, and the mixture evaporated in vacuo to give a solid, 3-amino-2-oxo-1-(sulfooxy)-1-azaspiro[3.3]heptane, which was triturated twice with hexane and dried in vacuo at 25° C. for 1 hour.

(Z)-2-Amino-α-[[[[(diphenylmethyl)oxy]carbonyl]methyl]oxy]imino]-4-thiazoleacetic acid, diphenylmethyl ester (0.42 g, 1.0 mmole) was dried for 2 hours at 25° C. in vacuo over phosphorous pentoxide. A solution of this solid in 5.0 ml of dry dimethylformamide under argon was treated with 0.10 g (1.0 mmole) of triethylamine and cooled to −35° C. Diphenylchlorophosphate (207 μl, 269 mg, 1.0 mmole) was added, and the mixture was stirred at −30° to −40° C. for 50 minutes, giving a yellow turbid solution of a mixed anhydride.

3-Amino-2-oxo-1-(sulfoxy)-1-azaspiro[3.3]heptane (from above) was taken up in 5 ml of dry dimethylformamide at 0° C., and this solution was added simultaneously to the mixed anhydride with 0.4 g (4 mmoles) of triethylamine. After 1 hour at −35° to −5° C., the dimethylformamide was evaporated in vacuo at 10° C. and the residue taken up in acetone and water, pH 4.35. Dilute potassium bicarbonate was used to adjust the pH to 6.75, and the solution was passed through a 30 ml Dowex AG50 (K+) column in 50% acetone-water. Product fractions were evaporated in vacuo to give a water slurry which was loaded on a 40 ml HP-20 column and eluted with water. Introduction of a 50% acetone gradient yielded the product. Lyophilization gave 400 mg of product as an off-white powder.

(G)

(Z)-[[[1-(2-Amino-4-thiazolyl)-2-oxo-2-[[2-oxo-1-(sulfooxy)-1-azaspiro[3.3]hept-3-yl]amino]ethylidene]amino]oxy]acetic acid, dipotassium salt (Z)-[[[1-(2-Amino-4-thiazolyl)-2-oxo-2-[[2-oxo-1-(sulfooxy)-1-azaspiro[3.3]hept-3-yl]amino]ethylidene]amino]oxy]acetic acid, diphenylmethyl ester, monopotassium salt (325 mg, 0.51 mmole) was slurried in a mixture of 6 ml of dry dichloromethane and 1 ml of anisole at −10° C. under argon, and treated with 10 ml of trifluoroacetic acid. After 45 minutes at −10° to 0° C., 10 ml of dry toluene was added, and the volatiles were evaporated in vacuo at 10° C. The residue was triturated twice with hexane, pumped dry in vacuo, then taken up in 10 ml of water (pH 1.8) and adjusted to pH 6.75 with dilute potassium bicarbonate. Chromatography on a 40 ml HP-20 column in water gave, after 140 ml of eluant, the product fractions. Lyophilization gave 205 mg of the title compound as a white solid.

Analysis Calc'd for $C_{13}H_{13}N_5O_9S_2K_2 \cdot 2.95H_2O$: C, 26.98; H, 3.29; N, 12.10; S, 11.08; K, 13.51. Found: C, 26.98; H, 2.68; N, 12.04; S, 10.81; K, 14.78.

EXAMPLE 3

(Z)-[[[1-(2-Amino-4-thiazolyl)-2-oxo-2-[[2-oxo-1-(sulfooxy)-7-oxa-1-azaspiro[3.5]non-3-yl]amino]ethylidene]amino]oxy]acetic acid (A)

N-(t-Butoxycarbonyl)-α-(4-hydroxy-2,3,5,6-tetrahydro-4-pyranyl)glycine, benzyl ester A solution of diisopropylamine (17.5 ml, 0.127 moles) in 300 ml of dry tetrahydrofuran at −45° C. under argon was treated with 70 ml (0.117 moles) of 1.71M n-butyllithium (in hexane). After 20 minutes at −45° C., the mixture was cooled to −72° C. and treated with 13.3 g (0.05 moles) of dried N-(t-butoxycarbonyl)glycine, benzyl ester in 60 ml of dry tetrahydrofuran. After 50 minutes, the dark yellow homogeneous solution was treated with 5 ml (5.43 g, 0.0543 moles) of tetrahydro-4-pyranone in 50 ml of tetrahydrofuran and the temperature allowed to rise to 0° C. over 1.5 hours. A solution of 7.2 g (0.12 moles) of glacial acetic acid in 20 ml of tetrahydrofuran was added to the purple solution, and the resulting light yellow turbid mixture was poured into 1L of water and extracted with ethyl acetate. The organic layer was washed with 2% potassium bisulfate, 5% sodium bicarbonate and brine, dried (sodium sulfate) and evaporated to an oil. Chromatography on 800 ml of LPS-1 in hexane:ethyl acetate (1:1) and combination of the product fractions (Rf=0.32 in the same solvent) gave an oil which solidified on trituration with hexane yielding a total of 10.34 g of product as a white solid, melting point 90°–93° C.

(B)

N-(t-Butoxycarbonyl)-α-(4-hydroxy-2,3,5,6-tetrahydro-4-pyranyl)glycine

N-(t-Butoxycarbonyl)-α-(4-hydroxy-2,3,5,6-tetrahydro-4-pyranyl)glycine, benzyl ester (10.34 g, 28.3 mmoles) and 10% palladium on charcoal (2.0 g) in 200 ml of absolute ethanol was treated with hydrogen at 1 atmosphere for 2 hours. The catalyst was filtered and the solvent removed in vacuo finally by co-evaporation with benzene. A small amount of ethyl acetate induced crystallization. The slurry was triturated with isopropyl ether, filtered and washed with isopropyl ether and hexane and dried in air to give 6.84 g of product as a white solid, melting point 140°–141° C.

(C)

N-(Benzyloxy)-$N^2$-(t-butoxycarbonyl)-α-(4-hydroxy-2,3,5,6-tetrahydro-4-pyranyl)glycinamide N-(t-Butoxycarbonyl)-α-(4-hydroxy-2,3,5,6-tetrahydro-4-pyranyl)glycine (6.84 g, 24.9 mmoles) and N-hydroxybenzotriazole hydrate (3.80 g, 24.9 mmoles) in 150 ml of tetrahydrofuran at 0° C. was treated with dicyclohexylcarbodiimide (5.12 g, 24.9 mmole) and stirred for 1 hour. To this was added a solution of O-benzylhydroxylamine in 50 ml of tetrahydrofuran. The resulting slurry was stirred for 14 hours at 0° to 25° C., then chilled to 0° C. and filtered. The filrate was evaporated to a foam. This was partitioned between ethyl acetate and 5% sodium bicarbonate. The organic layer was separated and washed with 3% potassium bisulfate, dried (sodium sulfate) and evaporated to a solid. Trituration with isopropyl ether and hexane gave 8.14 g of product, melting point 154°–157° C.

(D)

1-(Benzyloxy)-3-[(t-butoxycarbonyl)amino]-2-oxo-7-oxa-1-azaspiro[3.5]nonane

N-(Benzyloxy)-$N^2$-(t-butoxycarbonyl)-α-(4-hydroxy-2,3,5,6-tetrahydro-4-pyranyl(glycinamide (1.9 g, 5 mmoles) in 20 ml of dry pyridine under argon was treated with 1.05 g (6.5 mmoles) of pyridine-sulfur trioxide and heated to 57° C. for 2 hours. The volatiles were removed in vacuo. Dry acetonitrile was added and evaporated four times, and the residue was treated with a solution of 5 g (36 mmole) of potassium carbonate in 12.5 ml of water, followed by 40 ml of ethyl acetate. The mixture was heated to reflux with vigorous stirring for 6 hours. The mixture was cooled, diluted with water, and the layers separated. The organics were washed with 3% potassium bisulfate and brine, dried (sodium sulfate) and evaporated to a solid. Chromatography on 350 ml of LPS-1 in hexane:ethyl acetate (1:1) and evaporation of the pure product fractions (Rf=0.56 in same solvent) gave a solid. Trituration with isopropyl ether and air drying gave the product as a white solid, 0.78 g, melting point 144°–146° C.

(E)

3-[(t-Butoxycarbonyl)amino]-7-oxa-2-1-(sulfooxy)-1-azaspiro[3.5]nonane, monopotassium salt 1-(Benzyloxy)-3-[(t-butoxycarbonyl)amino]-2-oxo-7-oxa-1-azaspiro[3.5]nonane (0.78 g, 2.15 mmoles) was slurried in 20 ml of absolute ethanol and treated with 0.25 g of 10% palladium on charcoal and hydrogen at 1 atmosphere for 1 hour. The catalyst was filtered and volatiles removed in vacuo to give an oil. This was taken up in 15 ml of dry pyridine under argon and treated with 0.69 g (4.34 mmoles) of pyridine.sulfur trioxide at 25° C. for 3 hours. The volatiles were removed in vacuo, the residue taken up (partial solution) in water, and the pH adjusted to 6.75 with 5% potassium bicarbonate. The resulting slurry was poured onto a 20 ml Dowex AG50 (K+) column and completely eluted with water. Lyophilization gave a solid which was chromatographed on an 80 ml HP-20 column in a water-20% acetone:water gradient. Lyophilization of product fractions gave 0.64 g of product as a white solid.

(F)

(Z)-[[[1-(2-Amino-4-thiazolyl)-2-oxo-2-[[2-oxo-1-(sulfooxy)-7-oxa-1-azaspiro[3.5]non-3-yl]amino]ethylidene]amino]oxy]acetic acid, diphenylmethyl ester monopotassium salt 3-[(t-Butoxycarbonyl)amino]-7-oxa-2-oxo-1-(sulfooxy)-1-azaspiro[3.5]nonane, monopotassium salt (0.39 g, 1.0 mmole) was slurried at −10° C. under argon with 2.5 ml of dry dichloromethane and 1.0 ml of anisole. A 6 ml portion of trifluoroacetic acid was added. After 1 hour at −10° to 0° C., dry toluene (6 ml) was added and the mixture evaporated in vacuo at 10° C. Trituration with hexane gave 3-amino-7-oxa-2-oxo-1-(sulfooxy)-1-azaspiro[3.5]nonane as a white solid.

(Z)-2-Amino-α-[[[[(diphenylmethyl)oxy]carbonyl]methyl]oxy]imino]-4-thiazoleacetic acid (0.42 g, 1.0 mmole) in 4 ml of dry dimethylformamide was treated at −35 ° C. with 140 μl (1.0 mmole) of triethylamine, followed by 207 μl (1.0 mmole) of diphenyl chlorophosphate. After stirring for 1 hour, a solution of 3-amino-7-oxa-2-oxo-1-(sulfooxy)-1-azaspiro[3.5]nonane (from above) in 5 ml of dry dimethylformamide was added simultaneously with 550 μl (4 mmoles) of triethylamine. The volatiles were removed at 10° C. in vacuo, and the residue was dissolved in 20 ml of acetone and diluted to cloud with water. The pH was adjusted to 6.75 with dilute potassium bicarbonate, and the solution passed through Dowex AG50 (K+) in 50% acetone-water. Evaporation gave a slurry which was chromatographed on a 60 ml HP-20 column in water-50% acetone-water gradient. Product fractions were lyophilized to give the product as a white solid, 0.39 g.

(G)

(Z)-[[[1-(2-Amino-4-thiazolyl)-2-oxo-2-[[2-oxo-1-(sulfooxy)-7-oxa-1-azaspiro[3.5]non-3-yl]amino]ethylidene]amino]oxy]acetic acid (Z)-[[[1-(2-Amino-4-thiazolyl-2-oxo-2-[[2-oxo-1-(sulfooxy)-7-oxa-1-azaspiro[3.5]-non-3-yl-]amino]ethylidene]amino]oxy]acetic acid diphenylmethyl ester, monopotassium salt (0.39 g, 0.57 mmole) was slurried in 6 ml of dry dichloromethane and 1.5 ml of anisole at −10° C. under argon and treated with 10 ml of trifluoroacetic acid. After 1 hour, dry toluene (12 ml) was added and the volatiles were removed in vacuo at 10° C. The residue was washed twice with hexane, then taken up in water and the pH adjusted to 6.75 with dilute potassium bicarbonate. Chromatography on HP-20 in water gave product mixed with inorganics. The impure product was lyophilized, take up in water and the pH adjusted to 2.5 with dilute hydrogen chloride. Chromatography on HP-20 in a water-50% acetone:water gradient and lyophilization of the pure product fractions yielded the title compound as a white powder, 177 mg.

Analysis Calc'd for $C_{14}H_{17}N_5O_{10}S_2 \cdot 2.08H_2O$: C, 32.53; H, 4.13; N, 13.55. Found: C, 32.53; H, 3.52; N, 13.18.

EXAMPLE 4

[3S(Z),4S]-[[[1-(2-Amino-4-thiazolyl)-2-oxo-2-[[2-oxo-1-(sulfooxy)-6-thia-1-azaspiro[3.4]oct-3-yl]amino]ethylidene]amino]oxy]acetic acid, dipotassium salt

(A)

N-(t-Butoxycarbonyl)-α-(3-hydroxy-2,3,4,5-tetrahydro-3-thiofuranyl)glycine, benzyl ester A solution of 17.5 ml (0.125 moles) of diisopropylamine in 300 ml of dry tetrahydrofuran at −35° C. under argon was treated with 70 ml of 1.71M n-butyllithium in hexane (0.12 moles), stirred for 20 minutes, then chilled to −70° C. and treated with a solution of t-(butyloxycarbonyl) glycine benzyl ester (13.3 g, 0.03 moles) in 60 ml of tetrahydrofuran. After 45 minutes at −70° C., the dark yellow solution was treated with solution of 3-tetrahydro thiofuranone (5.0 g, 0.049 moles) in 50 ml of tetrahydrofuran. The solution was warmed to −10° C., whereupon the clear dark yellow darkened to a clear brown. After 20 minutes at −10° C., 7.2 g (0.12 moles) of glacial acetic acid in 20 ml of tetrahydrofuran was added, and the resulting turbid light yellow mixture poured into water (1 L) and extracted with ethyl acetate. The organic layer was washed with 5% sodium bicarbonate, dried (sodium sulfate) and evaporated to an oil. Chromatography in hexane:ethyl acetate (2:1) on 900 ml of LPS-1 gave partial separation of contaminants from product. Evaporation of fractions of intermediate polarity (Rf=0.22 to 0.60) and trituration with isopropyl ether gave a total of 6.61 g of product as a white solid, melting point 101°-102° C.

(B)

N-(t-Butoxycarbonyl)-α-(3-hydroxy-2,3,4,5-tetrahydro-3-thiofuranyl)glycine

A slurry of N-(t-butoxycarbonyl)-α-(3-hydroxy-2,3,4,5-tetrahydro-3-thiofuranyl)glycine, benzyl ester (2.65 g, 7.22 mmole) in 20 ml of water was treated with potassium bicarbonate (1.0 g, 7.8 mmole) followed by 15 ml of methanol. Stirring at 25° C. for 14 hours gave a homogeneous solution which was diluted with water and extracted with ethyl acetate. The aqueous layer was acidified with 10% potassium bisulfate, saturated with sodium chloride, and extracted with ethyl acetate. Drying (sodium sulfate) and evaporation of the organic layer, and trituration of the residue with isopropyl ether gave the product as a white solid, 1.25 g, melting point 116°–118° C.

(C)
N-(Triphenylmethoxy)-N$^2$-(t-butoxycarbonyl)-α-(3-hydroxy-2,3,4,5-tetrahydro-3-thiofuranyl)glycinamide A mixture of N-(t-butoxycarbonyl)-α-(3-hydroxy-2,3,4,5-tetrahydro-3-thiofuranyl)glycine (0.92 g, 3.32 mmole) and hydrated hydroxybenzotriazole (0.91 g, 3.33 mmole) in 30 ml of tetrahydrofuran at 0° C. was treated with dicyclohexylurea (0.68 g, 3.30 mmole). After 1 hour at 0° C., 0.91 g (3.30 mmole) of o-trityl hydroxylamine was added, and stirring continued at 0° to 25° C. for 18 hours. The slurry was evaporated in vacuo to a solid, then triturated with 300 ml of 2% methanol in dichloromethane and filtered. The filtrate was washed with 5% sodium hydroxide dried (sodium sulfate) and evaporated to a solid. A slurry of this solid was packed on an 800 ml LPS-1 column in 1% methanol/dichloromethane. Product was eluted with the same solvent, and pure fractions (Rf=0.46 in 2% methanol/dichloromethane) combined and evaporated to give the product as a white solid; 1.62 g, melting point 220°–225° C.

(D)
1-(Triphenylmethoxy)-3-[(t-butoxycarbonyl)amino]-2-oxo-6-thia-1-azaspiro[3.4]octane A solution of distilled 2-picoline (0.28 g, 3.0 mmole) in 2 ml of dry dichloromethane at −70° C. was treated with a solution of chlorosulfonic acid (0.14 g, 1.2 mmole) in 1 ml of dichloromethane, and the mixture warmed to 25° C. for one-half hour. To this homogeneous mixture was added a slurry of 0.53 g (1.0 mmole) of N-(triphenylmethoxy)-N$^2$-(t-butoxycarbonyl)-α-(3-hydroxy-2,3,4,5-tetrahydro-3-thiofuranyl)glycinamide in 5 ml of dichloromethane, and the mixture refluxed vigorously for 3 hours. The resulting clear solution was evaporated to dryness in vacuo, then covered with a mixture of water (2 ml), methyl isobutyl ketone (7 ml) and potassium carbonate (0.52 g, 3.8 mmoles). The mixture was refluxed with vigorous stirring under argon for 3 hours, cooled, the layers separated and the organics dried (sodium sulfate) and evaporated to a foam. Trituration with isopropyl ether gave a solid. This was taken up in hexane:ethyl acetate (2:1) and washed through a short pad of LPS-1. Evaporation and trituration with isopropyl ether gave 0.19 g of product as a white solid, melting point 204°–205° C.

(E)
3-[(t-Butoxycarbonyl)amino]-6-thia-2-oxo-1-hydroxy-1-azaspiro[3.4]octane

A slurry of 1-(triphenylmethoxy)-3-[(t-butoxycarbonyl)amino]-2-oxo-6-thia-1-azaspiro[3.4]octane (0.41 g, 0.79 mmoles) in 15 ml of 80% acetic acid (20% water) was stirred for 1 hour at 25° C. Evaporation in vacuo gave a white solid. This was taken up in ethyl acetate, washed with 5% sodium bicarbonate, and the aqueous layer separated. Saturation of the aqueous layer with sodium chloride and repeated ethyl acetate extractions were necessary to recover product. Drying (sodium sulfate), evaporation, and trituration with isopropyl ether and hexane gave 0.275 g of product, melting point 155°–157° C.

(F)
3-[(t-Butoxycarbonyl)amino]-6-thia-2-oxo-1-(sulfooxy)-1-azaspiro[3.4]octane, tetrabutylammonium salt 3-[(t-Butoxycarbonyl)amino]-6-thia-2-oxo-1-hydroxy-1-azaspiro[3.4]octane (0.23 g) was added to a previously prepared slurry of chlorosulfonic acid (0.31 g, 2.7 mmoles) and pyridine (0.5 g, 6.3 mmoles) in 8 ml of dichloromethane at 25° C., and stirred for 2½ hours. Then 6 ml of 10% potassium bisulfate and 0.34 g (1.0 mmole) of tetrabutylammonium hydrogen sulfate was added with shaking. The layers were separated and the aqueous layer was extracted four times with dichloromethane. The organics were dried (sodium sulfate), evaporated, covered with ethyl acetate at 0° C. for 16 hours, filtered, and evaporated to 0.63 g of product as a foam.

(G)
3-Amino-6-thia-2-oxo-1-(sulfooxy)-1-azaspiro[3.4]octane

A solution of 3-[(t-butoxycarbonyl)amino]-6-thia-2-oxo-1-(sulfooxy)-1-azaspiro[3.4]octane, tetrabutylammonium salt (0.63 g) in 5 ml of dichloromethane and 1 ml of anisole at 0° C. was treated with 4 ml of trifluoroacetic acid. After 1.75 hours, the resultant slurry was diluted with dichloromethane and filtered to give a white solid after washing with dichloromethane and ether. Air drying gave 110 mg of product, melting point 150°–155° C.

(H)
[3S(Z),4S]-[[[1-(2-Amino-4-thiazolyl)-2-oxo-2-[[2-oxo-1-(sulfooxy)-6-thia-1-azaspiro[3.4]-oct-3-yl]amino]ethylidene]amino]oxy]acetic acid, diphenylmethyl ester, monopotassium salt (Z)-2-Amino-α-[[[[(diphenylmethyl)oxy]carbonyl]methyl]oxy]imino]-4-thiazoleacetic acid (0.21 g, 0.5 mmoles) and triethylamine (0.053 g, 0.52 mmoles) in 3 ml of dry dimethylformamide at −40° C. under argon was treated with 0.134 g (0.5 mmoles) of diphenyl chlorophosphate and stirred for 1 hour at −40° to −20° C. To the resulting solution was added a solution of 3-amino-6-thia-2-oxo-1-(sulfooxy)-1-azaspiro[3.4]octane (0.11 g, 0.43 mmoles) in 1 ml of dimethylformamide followed by 0.1 g (1 mmole) of triethylamine. After 15 minutes at −15° C., the volatiles were removed in vacuo at 15° C., the resultant gum taken up in acetone and enough water added to give a cloudy mixture (pH=3.45), and the pH adjusted with potassium bicarbonate to 6.75. The mixture was passed through Dowex AG50 (K+) in acetone:water (1:1) and the eluant evaporated to a slurry. Chromatography on HP-20 using gradient elution with water-acetone and lyophilization of product fractions [Rf=0.7 in ethyl acetate-acetic acid: water:butanol (5:1:1:1)] gave product as a white solid, 0.21 g.

(I)
[3S(Z),4S]-[[[1-(2-Amino-4-thiazolyl)-2-oxo-2-[[2-oxo-1-(sulfooxy)-6-thia-1-azaspiro[3.4]oct-3-yl]amino]ethylidene]amino]oxy]acetic acid, potassium salt A slurry of [3S(Z),4S]-[[[1-(2-amino-4-thiazolyl)-2-oxo-2-oxo-1-(sulfooxy)-6-thia-1-azaspiro[3.4]-oct-3-yl]amino]ethylidene]amino]oxy]acetic acid, diphenylmethyl ester monopotassium salt (0.21 g, 0.3 mmole) in 8 ml of dichloromethane and 1.5 ml of anisole at −10° C. was treated with 8 ml of trifluoroacetic acid. After 15 minutes, 8 ml of dry toluene was added, and the mixture evaporated in vacuo at 15° C. The residue was washed with hexane. Addition of water gave an insoluble gum. The pH was adjusted from 1.50 to pH 6.75, giving a slightly turbid solution. Chromatography on HP-20 in water and lyophilization of the product fractions [Rf=0.25 in ethyl acetate:acetic acid:water:butanol (5:1:1:1)] gave product as a white solid, 118 mg. The product analyzed correctly for the presence of 2.55 moles of water.

Analysis Calc'd. for $C_{13}H_{13}N_5O_9S_3K_2 \cdot 2.55H_2O$: C, 25.87; H, 3.02; N, 11.60; S, 15.93; K, 12.96. Found: C, 25.86, H, 2.70; N, 11.48; S, 15.96; K, 13.31.

What is claimed is:

1. A compound having the formula

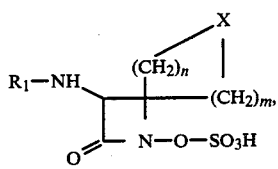

or a pharmaceutically acceptable salt thereof, wherein $R_1$ is acyl; and n and m are each independently 1, 2, 3 or 4, the sum of $n+m \leq 5$ and X is —O—, —S—, or

or n and m are each 1 and X is —S—CH$_2$—S—,

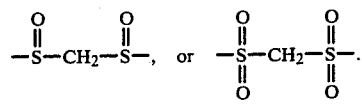

2. A compound in accordance with claim 1 wherein n and m are each independently 1, 2, 3 or 4, the sum of $n+m \leq 5$ and X is —O—, —S— or

3. A compound in accordance with claim 1 wherein n and m are each 1 and X is —S—CH$_2$—S—,

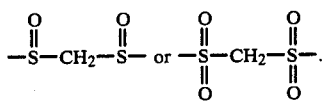

4. A compound in accordance with claim 1 wherein $R_1$ is

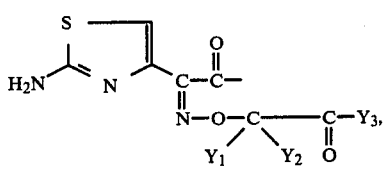

and $Y_1$ and $Y_2$ are each independently hydrogen or methyl or $Y_1$ and $Y_2$ together with the carbon atom to which they are attached are cyclopropyl, cyclobutyl or cyclopentyl, and $Y_3$ is hydroxy, amino or hydroxyamino.

5. The compound in accordance with claim 1, (Z)-[[[1-(2-amino-4-thiazolyl)-2-oxo-2-[[2-oxo-1-(sulfooxy)-7-oxa-1-azaspiro[3.5]non-3-yl]amino]ethylidene]amino]oxy]acetic acid or a salt thereof.

6. The compound in accordance with claim 1, [3S(Z),4S]-[[[1-(2-amino-4-thiazolyl)-2-oxo-2-[[2-oxo-1-(sulfooxy)-6-thia-1-azaspiro[3,4]oct-3-yl]amino]ethylidene]amino]oxy]acetic acid or a salt thereof.

* * * * *

UNITED STATES PATENT AND TRADEMARK OFFICE
CERTIFICATE OF CORRECTION

PATENT NO. : 4,680,388

DATED : July 14, 1987

INVENTOR(S) : Joseph E. Sundeen, William H. Koster, Robert Zahler

It is certified that error appears in the above-identified patent and that said Letters Patent is hereby corrected as shown below:

Column 22, line 46, "[3,4]" should be --[3.4]--.

Signed and Sealed this

First Day of March, 1988

Attest:

DONALD J. QUIGG

Attesting Officer     Commissioner of Patents and Trademarks